United States Patent
Tanzer

(10) Patent No.: US 6,610,900 B1
(45) Date of Patent: Aug. 26, 2003

(54) ABSORBENT ARTICLE HAVING SUPERABSORBENT IN DISCRETE POCKETS ON A STRETCHABLE SUBSTRATE

(75) Inventor: Richard Warren Tanzer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/385,228

(22) Filed: Aug. 27, 1999

(51) Int. Cl.[7] .............................................. A61F 13/15
(52) U.S. Cl. .................................. 604/368; 604/385.16
(58) Field of Search ........................... 604/385.16, 364, 604/367, 368

(56) References Cited

U.S. PATENT DOCUMENTS

| | | | |
|---|---|---|---|
| 3,901,236 A | 8/1975 | Assarsson et al. .......... 128/284 |
| 4,055,180 A | * 10/1977 | Karami ....................... 128/287 |
| 4,062,817 A | 12/1977 | Westerman .......... 260/17.45 G |
| 4,076,663 A | 2/1978 | Masuda et al. ...... 260/17.4 GC |
| 4,259,387 A | 3/1981 | Mesek ......................... 428/167 |
| 4,286,082 A | 8/1981 | Tsubakimoto et al. ...... 526/240 |
| 4,340,706 A | 7/1982 | Obayashi et al. ........... 526/207 |
| 4,578,068 A | * 3/1986 | Kramer et al. .............. 604/368 |
| 4,699,619 A | 10/1987 | Bernardin .................... 604/378 |
| 4,798,603 A | 1/1989 | Meyer et al. ............... 604/378 |
| 4,834,735 A | 5/1989 | Alemany et al. ........... 604/368 |
| 4,847,134 A | 7/1989 | Fahrenkrug et al. ........ 428/138 |
| 4,892,535 A | 1/1990 | Björnberg et al. |
| 5,147,343 A | 9/1992 | Kellenberger ............... 604/368 |
| 5,149,335 A | 9/1992 | Kellenberger et al. ...... 604/372 |
| 5,366,452 A | 11/1994 | Widlund et al. ......... 604/385.2 |
| 5,376,198 A | 12/1994 | Fahrenkrug et al. ........ 156/164 |
| 5,382,467 A | 1/1995 | Widlund et al. |
| 5,389,095 A | 2/1995 | Suzuki et al. ............. 604/385.2 |
| 5,411,497 A | 5/1995 | Tanzer et al. ............... 604/368 |
| 5,422,169 A | * 6/1995 | Roe ............................ 128/212 |
| 5,425,725 A | * 6/1995 | Tanzer et al. ............... 604/368 |
| 5,433,715 A | 7/1995 | Tanzer et al. ............... 604/368 |
| 5,451,219 A | 9/1995 | Suzuki et al. |
| 5,474,545 A | * 12/1995 | Chikazawa ................. 604/368 |
| 5,509,915 A | 4/1996 | Hanson et al. .............. 604/378 |
| 5,520,673 A | 5/1996 | Yarbrough et al. ......... 604/378 |
| 5,560,878 A | * 10/1996 | Dragoo et al. .............. 264/115 |
| 5,593,399 A | 1/1997 | Tanzer et al. ............... 604/368 |
| 5,601,542 A | 2/1997 | Melius et al. |

(List continued on next page.)

FOREIGN PATENT DOCUMENTS

| | | | |
|---|---|---|---|
| EP | 0 601 610 A1 | 6/1994 | |
| WO | 96/16624 | 6/1996 | ........... A61F/13/15 |
| WO | 98/37846 | 9/1998 | |

OTHER PUBLICATIONS

US 5,915,536, 6/1999, Alberts et al. (withdrawn)*

Primary Examiner—Dennis Ruhl
(74) Attorney, Agent, or Firm—Pauley Petersen Kinne & Erickson

(57) ABSTRACT

An absorbent article has a liquid permeable top sheet, a substantially liquid impermeable, preferably water vapor permeable back sheet, and a selectively stretchable absorbent composite between the top sheet and the back sheet. The selectively stretchable absorbent composite is more stretchable in a first direction than in a second direction perpendicular to the first direction, and can be stretched to at least 150% of an initial length in the first direction. The absorbent composite has a selectively stretchable substrate layer and a plurality of pockets in or on the substrate layer. The pockets each contain a quantity of superabsorbent material, which can swell when exposed to a liquid insult. When the substrate is stretched, the pockets become spaced further apart, thereby promoting comfort and alleviating gel blocking caused by adjacent pockets swelling toward each other.

33 Claims, 3 Drawing Sheets

U.S. PATENT DOCUMENTS

| | | | |
|---|---|---|---|
| 5,645,542 A | 7/1997 | Anjur et al. | 604/368 |
| 5,662,634 A | 9/1997 | Yamamoto et al. | 604/378 |
| 5,683,374 A | 11/1997 | Yamamoto et al. | 604/385.2 |
| 5,824,004 A * | 10/1998 | Osborn, III et al. | 604/385.2 |
| 5,846,232 A | 12/1998 | Serbiak et al. | 604/385.2 |
| 5,865,824 A | 2/1999 | Chen et al. | |
| 5,882,769 A | 3/1999 | McCormack et al. | |
| 5,883,028 A | 3/1999 | Morman et al. | 442/394 |
| 5,904,675 A | 5/1999 | Laux et al. | 604/385.2 |
| 5,910,224 A | 6/1999 | Morman | |
| 6,059,764 A * | 5/2000 | Osborn, III et al. | 604/385.2 |
| 6,061,840 A * | 5/2000 | Alligator | 2/403 |
| 6,264,641 B1 * | 7/2001 | Van Gompel et al. | 604/385.22 |

\* cited by examiner

ABSORBENT ARTICLE HAVING SUPERABSORBENT IN DISCRETE POCKETS ON A STRETCHABLE SUBSTRATE

FIELD OF THE INVENTION

This invention relates to an absorbent article in which superabsorbent material is contained in discrete pockets on a selectively stretchable substrate. The pockets may be present in one or more layers. When the superabsorbent material becomes wet, the resulting expansion causes adjacent pockets to engage and press against each other. The selectively stretchable substrate permits the expanding pockets to push each other apart in a selected direction. Furthermore, when the absorbent layer is stretched in the selected direction the pockets are increasingly separated from each other.

BACKGROUND OF THE INVENTION

Absorbent composites suitable for use in disposable absorbent garments such as diapers, adult incontinent products, and the like, are known. Such absorbent composites are described, for example, in U.S. Pat. No. 4,699,619 issued Oct. 13, 1987 to Bemardin, U.S. Pat. No. 4,798,603 issued Jan. 17, 1989 to Meyer et al., U.S. Pat. No. 4,834,735 issued May 30, 1989 to Alemany et al., U.S. Pat. No. 5,147,343 issued Sep. 15, 1992 to Kellenberger, and U.S. Pat. No. 5,149,335 issued Sep. 22, 1992, to Kellenberger et al.

Generally, such absorbent composites comprise a matrix for containing a high-absorbency material. Suitable matrices for containing the high-absorbency material include fibrous matrixes, such as those formed from air-laid cellulosic fibers or a coform material comprising cellulosic fibers and melt-blown polyolefin fibers. A wide variety of high absorbency materials (also known as superabsorbent materials) are known to those skilled in the art. See, for example, U.S. Pat. No. 4,076,663 issued Feb. 28, 1978 to Masuda et al, U.S. Pat. No. 4,286,082 issued Aug. 25, 1981 to Tsubakimoto et al., U.S. Pat. No. 4,062,817 issued Dec. 13, 1977 to Westerman, and U.S. Pat. No. 4,340,706 issued Jul. 20, 1982 to Obayashi et al.

Many known absorbent composites comprising a high-absorbency material employ the high-absorbency material in relatively low concentrations. That is, many of the absorbent composites comprise air-laid cellulosic fibers and less than about 20 weight percent of high-absorbency material. This is due to several factors.

Many high-absorbency materials are unable to absorb a liquid at the rate at which the liquid is applied to the absorbent composites during use. Accordingly, a relatively high concentration of fibrous material is desirable to temporarily hold the liquid until the high-absorbency material can absorb it. Further, the fibers serve to separate the particles of high-absorbency material so that gel-blocking does not occur. Gel-blocking refers to the situation wherein particles of high-absorbency material deform during swelling and block the interstitial spaces between the particles, or between the particles and fibers, thus preventing the flow of liquid through the interstitial spaces.

The presence of a relatively low concentration of high-absorbency material and a relatively greater concentration of fibrous materials has resulted in the production of absorbent composites which tend to be relatively thick. In some instances, the use of a relatively thick absorbent composite in a disposable absorbent garment is acceptable. However, in recent years it has become increasingly desirable to produce absorbent composites which are thin compared to the more traditional absorbent composites but which still possess the same absorbent capacity. The desire to produce relatively thin absorbent composites has resulted in the desire to incorporate ever-increasing amounts of high-absorbency material into the absorbent composites. This is because the absorbent capacity of such high-absorbency materials is generally many times greater than the absorbent capacity of fibrous materials. For example, a fibrous matrix of wood pulp fluff can absorb about 7–9 grams of a liquid, (such as 0.9 weight percent saline) per gram of wood pulp fluff, while the high-absorbency materials can absorb at least about 15, preferably at least about 20, and often at least about 25 grams of liquid, such as 0.9 weight percent saline, per gram of the high-absorbency material.

A trend toward more stretchable diapers is illustrated in U.S. Pat. No. 5,846,232 issued to Serbiak et al., and in U.S. Pat. No. 5,451,219 issued to Suzuki et al. These references disclose various elastic or extensible structures in the diapers to achieve stretchability.

U.S. Pat. No. 5,601,542, issued to Melius et al., discloses an absorbent article in which superabsorbent material is contained in layers of discrete pouches. The pouches are adjacent one another, and are formed in one or more substrate layers. When the superabsorbent material becomes wet, the substrates either do not stretch or stretch uncontrollably in all directions. In the former case, the absorbent capacity of the superabsorbent may be inhibited because of the externally applied pressure of the substrates working against the swelling pressure of the superabsorbent. In the latter case, the uncontrolled stretching of the substrate can cause the wet superabsorbent gel to shift, reducing the effectiveness of the absorbent system, and causing discomfort to the wearer.

SUMMARY OF THE INVENTION

The present invention is an absorbent article having at least one absorbent composite which is selectively stretchable in one direction, wherein superabsorbent material is present in discrete pockets or pouches in or on a selectively stretchable substrate. The absorbent article includes at least a substantially liquid impermeable, vapor permeable back sheet, a liquid permeable top sheet positioned in facing relation with the back sheet, and one or more of the selectively stretchable absorbent layers between the top sheet and the back sheet.

The substrate in the absorbent composite is selectively stretchable in one direction. For instance, the substrate in a diaper product may be laterally stretchable between the legs of the wearer, without being longitudinally stretchable between the waist regions of the wearer. In one embodiment, the substrate may be a neck-bonded laminate of a necked, inelastic nonwoven filament web to an elastic film. Neck-bonded laminates of this type are described in U.S. Pat. No. 5,883,028, issued to Morman et al., the disclosure of which is incorporated by reference. Other suitable substrates include without limitation necked spunbond webs and necked, creped spunbond webs.

In one embodiment, the selectively stretchable substrate may comprise two layers of material which are joined together to form a plurality of pockets between them. The pockets may be formed in one or both layers. At least one of the layers should be water-pervious. The other layer may be water-pervious or water-impervious. The absorbent composite may also contain two of the selectively stretchable substrates, joined together with a plurality of pockets between them. In either case, the superabsorbent material is located in the pockets.

During use of the absorbent article, the pockets maintain the desired distribution of the superabsorbent material in the absorbent composite. The selectively stretchable substrate permits stretching of the absorbent layer in a desired direction, to accommodate movement of the wearer as well as swelling of the superabsorbent when wet. The absorbent composite can be used in a wide variety of absorbent articles including, for instance, personal care absorbent products and medical absorbent products. Personal care absorbent products include diapers, training pants, swim wear, absorbent underpants, baby wipes, adult incontinence garments and feminine hygiene products. Medical absorbent products include absorbent garments, underpads, bandages, absorbent drapes, and medical wipes.

With the foregoing in mind, it is a feature and advantage of the invention to provide an absorbent article which has a relatively stretchable absorbent composite and a distribution of pockets containing superabsorbent material, to alleviate gel blocking.

It is also a feature and advantage of the invention to provide an absorbent article having a selectively stretchable absorbent composite which preferentially stretches in a desired direction.

The foregoing and other features and advantages will become further apparent from the following detailed description of the presently preferred embodiments. The detailed description is illustrative rather than limiting, the scope of the invention being defined by the appended claims and equivalents thereof.

DETAILED DESCRIPTION OF THE PRESENTLY PREFERRED EMBODIMENTS

The present invention is an absorbent article having an absorbent composite layer which is selectively stretchable, wherein superabsorbent material is present in discrete pockets or pouches in or on a selectively stretchable substrate. The term "absorbent article" includes without limitation diapers, training pants, swim wear, absorbent underpants, baby wipes, adult incontinence products, feminine hygiene products and medical absorbent products (for example, absorbent medical garments, underpads, bandages, drapes, and medical wipes).

Figure 1:
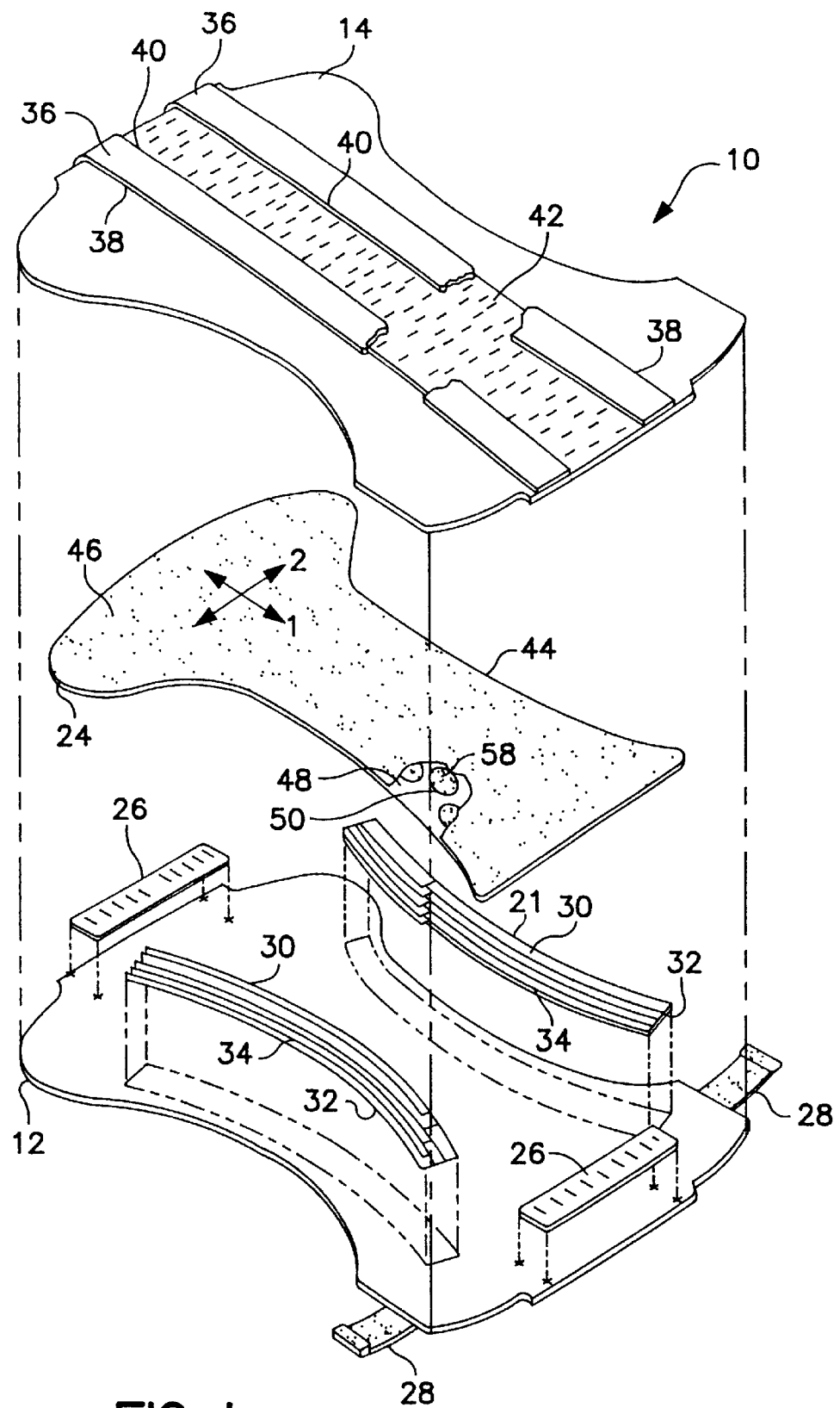
FIG. 1 is an exploded perspective view of one embodiment of an absorbent article of the invention, which is a disposable diaper.

One preferred absorbent article is a disposable diaper. FIG. 1 illustrates an exploded perspective view of a disposable diaper according to one embodiment of the present invention having a longitudinal direction 1 and a lateral direction 2. Disposable diaper 10 includes an outer cover 12, a body-side liner 14, and an absorbent composite 44 located between the body-side liner 14 and the outer cover 12. The absorbent composite 44 comprises a plurality of pockets 50 containing a superabsorbent material 58 and, optionally, wood pulp fibers as further described below. The absorbent composite also includes a two-piece wrap sheet comprising first substrate sheet layer 46 and second substrate sheet layer 48 described further below. The two-piece wrap sheet extends to the edges of the absorbent composite 44 and beyond the pockets 50, to define perimeter 24 which can be sealed to prevent superabsorbent material 58 from migrating out of the diaper.

Attached between outer cover 12 and body-side liner 14 are waist elastics 26, fastening tapes 28 and leg elastics 30. The leg elastics 30 comprise a carrier sheet 32 and individual elastic strands 34 having proximal edges 19 and distal edges 21.

Attached to the body-side liner 14 are containment flaps 36 having proximal edges 38 and distal edges 40. The proximal edges of the leg elastics correspond to the distal edges of the containment flaps. A surge management layer 42 having perimeter 43 is located between the proximal edges 38 of the containment flaps 36.

Many of the exact construction methods and materials of the diaper illustrated in FIG. 1 are set forth in greater detail in commonly assigned U.S. Pat. No. 5,509,915, issued Apr. 25, 1996 in the name of Hanson et al., and in U.S. Pat. No. 5,904,675, issued May 19, 1999 to Laux et al., both of which are incorporated herein by reference. Possible modifications to the diaper illustrated in FIG. 1 include positioning the surge management layer 42 between the body-side liner 14 and the absorbent composite 44 and reducing the length of the surge management layer to extend the length of the absorbent composite, or massing (reduce length and increase basis weight) the surge management layer in the area of the diaper where liquid waste initially accumulates (target zone).

Figure 2:
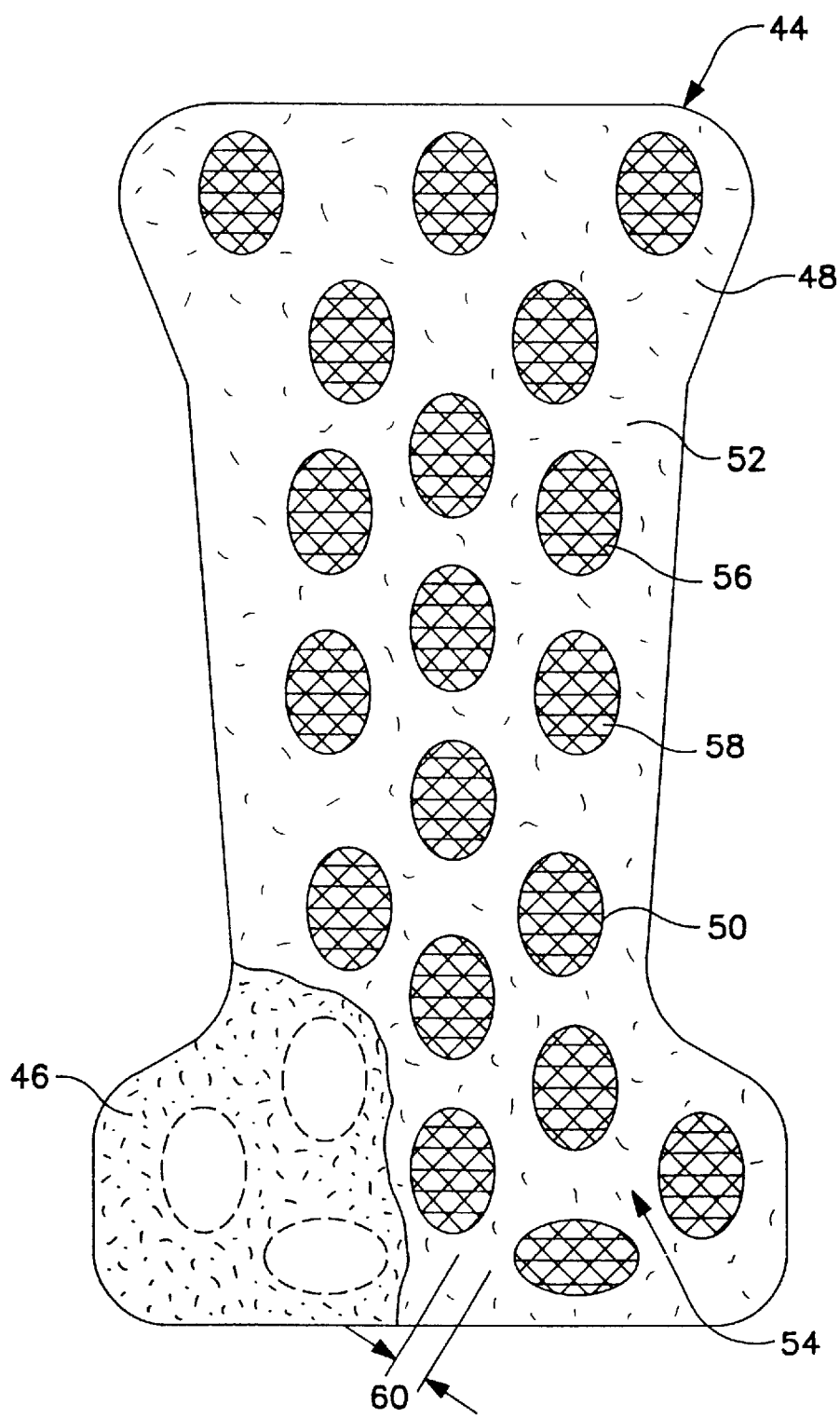
FIG. 2 is a cut away plan view of an absorbent composite useful in the article of FIG. 1.

FIG. 2 illustrates a selectively stretchable absorbent composite according to the present invention. With reference to FIG. 2, the absorbent composite 44 comprises a selectively stretchable liquid permeable first substrate layer 46, a selectively stretchable second substrate layer 48 and pockets 50 of superabsorbent material formed between the first layer 46 and second layer 48.

As used herein, the term "selectively stretchable" means that a material is more stretchable in a first direction than in a second direction, that is, can be stretched to a greater degree without breaking in the first direction than in the second direction. The second direction is perpendicular to the first direction. Generally, the material is stretchable to at least 150% of its initial length in the first direction, suitably to at least 200% of its initial length in the first direction, desirably to at least 250% of its initial length in the first direction. Generally, the material is stretchable to less than 140% of its initial length in the second direction, suitably to less than 125% of its initial length in the second direction, desirably to less than 110% of its initial length in the second direction.

The pockets 50 are defined by attachment means 52 which serve to operatively join the first and second layers to form a laminate and to maintain the integrity of the laminate when the laminate is dry but to controllably release them when the laminate becomes wetted. Alternatively, pockets 50 may be molded (e.g., thermoformed) into layer 46 or layer 48. Suitable attachment means between layers 46 and 48 include water sensitive adhesives, such as water soluble adhesives and thermal embossing. The attachment means 52 secures together the first layer 46 and the second layer 48 to provide attached zones 54 between pockets 50, and unattached zones 56 at pockets 50. The unattached zones help define pockets

50. A superabsorbent material 58 is located in the pockets 50 to provide absorbent composite 44. In addition to the superabsorbent material 58, the pockets 50 may contain a fibrous material such as cellulose fluff or another material, as discussed further below. A secondary attachment means (not shown), which is water insensitive, may also be employed to secure layers 46 and 48 together at locations spaced from pockets 50.

The pockets 50 are spaced by a distance 60 when the composite 44 is relaxed, i.e., is not subject to a stretching force. The spacing 60 is at least about 0.05 inch (1.3 mm), alternatively at least about 0.10 inch (2.5 mm) or alternatively at least about 0.15 inch (3.8 mm). Moreover, the pocket spacing 60 is suitably not more than about 1.5 inch (38 mm), alternatively not more than about 1.0 inch (25 mm), or alternatively not more than about 0.5 inch (13 mm).

The depth of pockets 50 may be at least about 0.1 inch (2.5 mm), preferably about 0.15–0.50 inch (3.8–13 mm), more preferably about 0.20–0.30 inch (5.1–7.6 mm). The pockets may have a circular or elliptical configuration, with diameters ranging from about 0.20–1.0 inch (5.1–25 mm), preferably about 0.25–0.75 inch (6.4–19.1 mm), more preferably about 0.40–0.60 inch (10.2–15.2 mm). These dimensions refer to the relaxed, unstretched state of absorbent composite 44.

In accordance with the invention, the absorbent composite 44 should be stretchable in a first direction, and not stretchable in a second direction perpendicular to the first direction. By "stretchable" it is meant that the composite 44 stretches to at least 150% of its initial length in the first direction without breaking, preferably to at least 200% of its initial length, more preferably to at least 250% of its initial length. Preferably, the absorbent composite is at least partially retractable in the direction opposite to the direction of stretching. Thus, when the force causing the stretching is relaxed, the stretched composite should recover or "retract" by at least 25%, preferably by at least 50%, more preferably by at least 75%. A "50% recovery", for example, means that when a material is stretched from an initial length of one meter to a stretched length of two meters, it should recover to a length of 1.5 meters when the stretching force is removed. The stretchability of absorbent composite 44 is generally controlled by the stretchability of the combined substrate layer or layers 46 and 48.

The absorbent composite 44 should be less stretchable in a second direction which is perpendicular to the first direction. By "not stretchable" or "less stretchable", it is meant that the composite 44 stretches to less than 150% of its initial length in the second direction before breaking, preferably to less than 125% of its initial length, more preferably to less than 110% of its initial length.

Certain materials, lightly bonded nonwovens, for example, do not necessarily have a distinct breaking point when stretched. The force required to elongate such materials increases to a maximum and then gradually declines as the elongation continues, rather than abruptly drop to zero when the material breaks. Such behavior may be characterized as "taffy-like."

As certain nonwovens are stretched, the fibers shift and gradually orient themselves in the direction that the material is being pulled. As stretching continues the fibers may slip out of the nonwoven matrix gradually reducing the force required to achieve further stretching.

Absorbent composites which exhibit taffy-like behavior in a first direction, do not necessarily exhibit taffy-like behavior in a second direction perpendicular to the first direction.

By "stretchable" absorbent composites which exhibit taffy-like behavior in at least one direction it is meant that the maximum force required to stretch composite 44 to 150% of its initial length is less than the maximum force required to stretch it in the perpendicular direction to 125% of its initial length. Preferably, the maximum force required to stretch the composite to 200% of its initial length is less than the maximum force required to stretch it in the perpendicular direction to 125% of its initial length. More preferably, the maximum force required to stretch the composite to 250% of its initial length is less than the maximum force required to stretch it in the perpendicular direction to 125% of its initial length.

Correspondingly, by "not stretchable" composites which exhibit taffy-like behavior in at least one direction it is meant that the maximum force required to stretch composite 44 to 150% of its initial length is at least equal to the maximum force required to stretch it in the perpendicular direction to 125% of its initial length.

The tensile stress-strain measurements required to determine the forces on these taffy-like composites will be conducted using International Standard ISO 1924-2:1994 (E), Paper and board—Determination of tensile properties—Part 2: Constant rate of elongation method, or similar methods.

The absorbent composite 44 is oriented in the absorbent article so that the direction of selective stretching corresponds to a direction where the article may desirably be stretched. In a diaper, for instance, the direction of preferred stretching may be lateral, from one leg to the other of the wearer. This permits the wearer to move his or her legs freely without experiencing discomfort. In this instance, the direction of preferred no stretching, or less stretching, may be from front to back, between the waist areas of the wearer. Alternatively, a diaper may be configured such that longitudinal stretching of the absorbent is preferred. To provide enhanced fit for instance, a diaper may gently stretch in the longitudinal direction to fit the baby.

Figure 3:
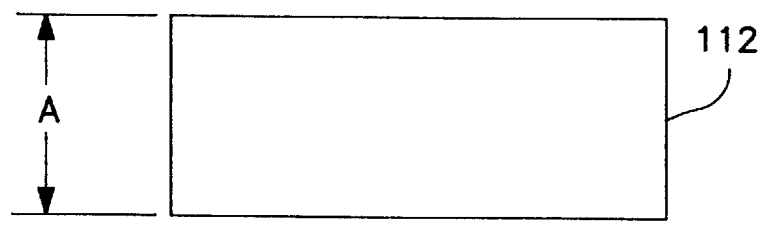
FIGS. 3, 3A and 3B schematically illustrate the formation of a neck-bonded laminate useful as a substrate in the absorbent composite.
Figure 3A:
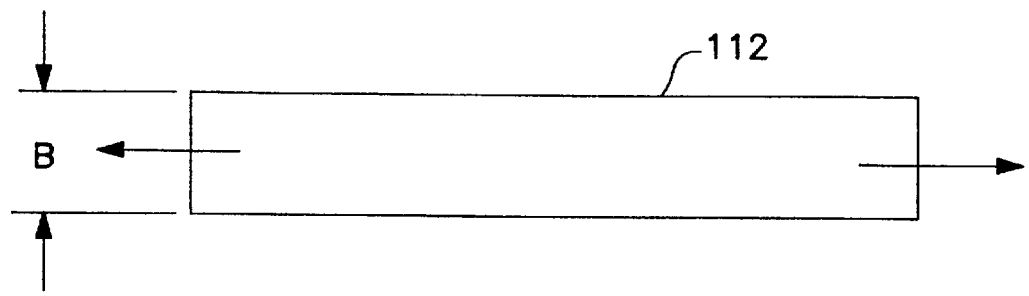
Figure 3B:
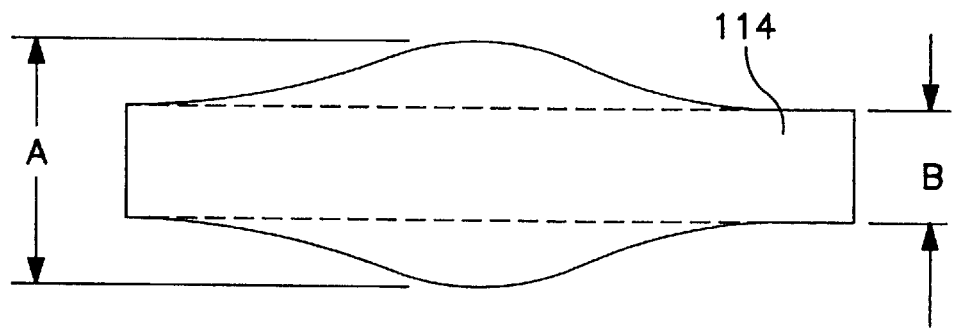

FIGS. 3, 3A and 3B schematically illustrate the formation of a neck-bonded laminate which may be employed as the first substrate layer 46 and/or the second substrate layer 48 of the absorbent composite 44. FIG. 3 illustrates a neckable material 112 which can, for instance, be a fibrous nonwoven web made of a relatively inelastic polymer material. Referring to FIG. 3B, the neckable material 112 is first pulled in a machine direction, causing its fibers to longitudinally orient and causing its length in the cross direction to contract from a first dimension "A" to a second dimension "B". At that point, the neckable nonwoven web 112 is laminated to an unstretched elastic film or other layer material, for instance using techniques described in U.S. Pat. No. 5,883,028, issued to Morman et al., which is incorporated by reference. The term "elastic" refers to a stretchable material which mostly recovers to its initial length when a stretching force is relaxed.

The resulting laminate 114, shown in FIG. 3B, has a relaxed length in the cross-machine direction which is substantially equal to the dimension "B". The laminate can be selectively stretched only in the cross-machine direction of the web 112, to a second length substantially equal to the dimension "A". When the stretching force is relaxed, the laminate 114 retracts to its original dimension "A".

The neckable web 112 may be a porous nonwoven material such as, for example, spunbonded web, meltblown web or bonded carded web. If the neckable material is a web of meltblown fibers, it may include meltblown microfibers.

The neckable material 112 may be made of fiber forming polymers such as, for example, polyolefins. Exemplary polyolefins include one or more of polypropylene, polyethylene, ethylene copolymers, propylene copolymers, and butene copolymers. Useful polypropylenes include, for example, polypropylene available from the Exxon Chemical Company under the trade designation Exxon 3445, and polypropylene available from Shell Chemical Company under the trade designation DX 5A09.

The neckable web 112 may be a multilayer material having, for example, at least one layer of spunbonded web joined to at least one layer of meltblown web, bonded carded web or other suitable material. For example, neckable material 112 may be a multilayer material having a first layer of spunbonded polypropylene having a basis weight from about 0.2 to about 8 ounces per square yard (osy) (about 6.8–270 grams/$M^2$, or gsm), a layer of meltblown polypropylene having a basis weight from about 0.2 to about 4 osy (6.8–135 gsm), and a second layer of spunbonded polypropylene having a basis weight of about 0.2 to about 8 osy (6.8–270 gsm). Alternatively, the neckable web 112 may be a single layer of material such as, for example, a spunbonded web having a basis weight of from about 0.2 to about 10 osy (6.8–340 gsm) or a meltblown web having a basis weight of from about 0.2 to about 8 osy (6.8–270 gsm). The adjacent fibers of web 112 should be intermittently joined by inter-fiber bonding, using conventional techniques known in the art.

An elastic sheet may be joined to the neckable web 112 when the latter is in the tensioned, necked state to form the neck-bonded laminate 114. The elastic sheet may be made from a water vapor permeable elastic polymer, or may be made from another elastic polymer and rendered vapor permeable by forming apertures or micropores in the sheet. Preferably, the elastic sheet has a moisture vapor transmission rate (MVTR) of at least about 500 grams/$m^2$–24 hours, more preferably at least about 1200 grams/$m^2$–24 hours, most preferably at least about 2000 grams/$m^2$–24 hours using the test procedure described below. The MVTR is a function of both film thickness and polymer type. Elastic polymers which exhibit the required MVTR over a range of useful film thicknesses include without limitation vulcanized silicone rubber, some other silicone polymers, polyurethanes, polyether esters and polyether amides. The following Table 1 gives representative water vapor permeabilities of exemplary elastic polymers, normalized to account for film thickness of a pure

TABLE 1

| Polymer Type | Water Vapor Permeability, kg-cm/$(km)^2$-day |
| --- | --- |
| Vulcanized silicone rubber | 11,900 |
| Polyurethane-Estane ® 58237 | 760 |
| Polyurethane-Estane ® 58245 | 1,270 |
| Polyether amide-PEBAX ® | 830 |
| Polyether ester Hytrel ® or Arnitel ® | 930 |
| Polyester-polyurethane copolymer | 160 |
| Polyether-polyurethane copolymer | 310 |

If the elastic polymer has low water vapor permeability, the film may have to be extremely thin in order to achieve the desired minimum level of MVTR. Elastomers having lower vapor permeability include, for instance, styrene-butadiene copolymers and terpolymers, elastomeric ethylene-propylene copolymers, ethylene-propylene diene rubbers, and certain single-site or metallocene-catalyzed ethylene polymers and ethylene-alpha olefin copolymers having a density not exceeding 0.89 grams/cc. Alternatively, the film may be rendered porous or microporous using numerous techniques familiar to persons skilled in the art. The production and use of very thin films may be impractical due to low film strength and processing difficulties. The elastic polymer itself should therefore have sufficient water vapor permeability to allow the use of films having practical thicknesses. Preferably, the elastic polymer will have a water vapor permeability of at least about 150 kg-cm/$(km)^2$–day, more preferably at least about 500 kg-cm/$(km)^2$–day, most preferably at least about 1000 kg-cm/$(km)^2$–day.

In addition to being water vapor permeable, the preferred breathable elastic film should not be so thick as to substantially impair its water vapor transmission. The MVTR of a particular composition of film is roughly inversely related to its thickness if there are no molecular interactions between the film and the vapor. For water vapor permeable films, this relationship may vary due to the affinity of the water with the films. Generally, the elastic film component of neck-bonded laminate 114 should be less than about 2 mils (50 microns) thick, preferably less than about 1 mil (25 microns) thick, more preferably less than about 0.5 mil (13 microns) thick, when the film and laminate 114 are relaxed.

Referring to FIG. 2, when a neck-bonded laminate is used as the substrate in absorbent composite 44, the top (liquid permeable) layer 46, which faces the wearer, may be a necked, nonwoven layer and the bottom layer 48 may be an elastic film or sheet, of the neck-bonded laminate. Alternatively, the bottom layer 48 may include an entire neck-bonded laminate (film and necked nonwoven web), and the top layer 46 may be another nonwoven or other liquid-pervious layer, such as a nonwoven spunbond layer. The layers 46 and 48 may be bonded together using a wide variety of conventional techniques, including adhesive bonding, thermal bonding, ultrasonic bonding and the like. Preferably, the bonded area constitutes about 10–20% of the interface between layers 46 and 48. In one preferred embodiment, a stretchable hot melt adhesive 25 or 25A available from Findlay Adhesives Co. is applied in a swirl pattern covering 10–20% of the interface.

Pockets 50 may be formed in layer 46 or layer 48, and are preferably formed in bottom layer 48. Pockets 50 may be formed using a vacuum thermoforming process or another suitable process. In one embodiment, the pocket forming, superabsorbent application and bonding are performed in an integrated process. Initially, a selectively stretchable material 46 such as a neck-stretched spunbond material, is positioned over a perforated plate having pocket-shaped depressions. Vacuum is applied to the plate, causing the material to be pulled into pocket-shaped depressions. A superabsorbent is then added to each pocket, and an adhesive is applied to layer 46. Then top layer 48, which is liquid pervious, is positioned over layer 46 and its pockets, and pressed. The layers 46 and 48 are thus bonded by action of the adhesive.

In still another embodiment, one of the substrate layers 46 or 48 may be eliminated. If top substrate layer 46 is eliminated, the liquid-permeable body-side liner 14 may act as a top substrate layer in cooperation with substrate layer 48. If substrate layer 48 is eliminated, the liquid-impermeable, vapor permeable outer cover 12 may act as a lower substrate layer in cooperation with substrate layer 46. If either the body-side line 14 or outer cover 12 is used as a substrate, then it should be rendered selectively stretchable as described herein for the substrate layers.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. INDA Standard Test Method IST 10.1 (95), "Standard Test Method for Absorbency Time, Absorbency Capacity, and Wicking Time," published by INDA, Association of the Nonwoven Fabrics Industry, Cary, N.C., provides the basis for a suitable test method to measure absorbency. The "Absorptive Capacity Test (for small specimens)" may be used to determine the absorbency of a material for the purpose of the subject invention with the following two modifications: (i) IST 10.1 (95) specifies that water is to be used; substitute a 0.9% aqueous solution, (ii) IST 10.1 (95) specifies that a 5 gram sample is used. If necessary, a smaller sample, obtained from an absorbent product may be used instead.

The superabsorbent materials can be natural, synthetic, and modified natural polymers and materials. In addition, the superabsorbent materials can be inorganic materials, such as silica gel, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations of Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic super-absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbents may be particulate or fibrous, and are preferably particulate. Superabsorbents are generally available in particle sizes ranging from about 20 to about 1000 microns. Preferred particle sizes range from 100 to 1000 microns. Examples of commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® 880 available from Stockhausen, located in Sweden. FAVOR® 880 is presently preferred because of its high gel strength. An example of a fibrous superabsorbent is OASIS® 101, available from Technical Absorbents, located in Grimsby, United Kingdom.

Depending on the size of pockets 50, and density of the superabsorbent, each pocket may contain about 25–500 mg of superabsorbent material, based on its dry weight, preferably about 50–300 mg, more preferably about 100–200 mg.

The number and size of pockets 50 may be such that selectively stretchable absorbent composite 44 contains about 1–100 grams of total superabsorbent, preferably about 3–50 grams, more preferably about 5–15 grams. Of course, the total amount of superabsorbent may vary depending on the size of the absorbent article. Furthermore, more than one selectively stretchable absorbent composite 44 may be present in an absorbent article, and two or more selectively stretchable absorbent composites 44 may be superimposed over each other.

In addition to the superabsorbent material, each pocket 50 may contain, if desired, a fibrous absorbent material such as pulp fibers, a filler material, an odor absorbent material, a fragrant material, or another suitable material. When combinations of materials are employed, the superabsorbent should constitute at least 30% of the total material in pockets 50, preferably at least 50%, more preferably at least 70%, most preferably at least 90%. Alternatively, some of the pockets, preferably fewer than 50%, may contain no superabsorbent. The pockets without superabsorbent may contain only odor absorbent materials, fragrances, lotions, emollients, antimicrobials and the like.

The selective stretchability of the absorbent composite 44 permits a high concentration of superabsorbent to be contained in pockets 50, without resulting in gel blocking, when the composite becomes wet. As the superabsorbent becomes wet and the pockets expand toward each other, the selective stretchability of the composite 44 permits movement of the pockets, thus preventing their contact from becoming so tight that gel blocking occurs.

Preferably, the pockets 50 have a shape which permits them to touch each other without closing all of the space between them. When viewed in plan, as in FIG. 2, pockets 50 have a circular, oval or elliptical shape. Pockets having these shapes are also less likely to rupture under forces of superabsorbent swelling and stretching, and forces applied during product manufacture. Square and rectangular shapes are less preferred, because these shapes would permit substantially continuous contact along the edges of adjacent pockets 50. Also, pockets having these shapes are more likely to rupture when under stress.

The absorbent composite 44 may be joined to the outer cover 12 and body-side liner 14 (FIG. 1) using a variety of techniques including thermal bonding, ultrasonic bonding, mechanical stitch bonding, adhesive bonding, and the like. In order to achieve optimum performance, it is desired that the selective stretchability of the absorbent composite 44 be allowed to control the stretchability of the entire diaper 10. This can be accomplished by forming the other layers of diaper 10 from materials that are at least as stretchable as absorbent composite 44. The body-side liner 14 and outer cover 12 need not be selectively stretchable. They can be uniformly stretchable in all directions, and can be formed using one or more of the elastic polymers described above. As long as the materials forming layers 12 and 14 (and any other layers) are at least as stretchable as absorbent composite 44, the entire diaper 10 will exhibit selective stretching influenced by absorbent composite 14.

Both the surge layer 42 and body-side liner 14 are constructed from highly liquid pervious materials. These layers function to transfer liquid from the wearer to the absorbent composite 44. Suitable materials include porous woven materials, porous nonwoven materials, and apertured films. Examples include, without limitation, any stretchable porous sheets of polymeric fibers, bonded carded webs of synthetic or natural fibers or combinations thereof. Either layer may also be an apertured stretchable plastic film.

The outer cover 12 may include a single stretchable layer, or may include multiple stretchable layers joined together by adhesive bonding, ultrasonic bonding, thermal bonding or the like. Outer cover 12 can be made from a wide variety of woven or nonwoven material, films, or a film-coated nonwoven material, including, for instance, cast or blown films. Outer cover 12 may also be a composite of a bonded carded or spunbonded or meltblown material, for example, a spunbonded-meltblown composite of thermoplastic material or a spunbonded-meltblown-spunbonded thermoplastic material, wherein the spunbonded layer can provide a cloth-like texture and the meltblown layer can provide liquid impermeability. Outer cover 12 is preferably highly breathable to water vapor.

Test Procedure for Measuring Moisture Vapor Transmission Rate (MVTR)

A measure of the breathability of a fabric is the moisture vapor transmission rate (MVTR), which for the sample materials is calculated essentially in accordance with ASTM Standard E96-80 with minor variations in test procedure as set forth below. Circular samples measuring three inches in diameter are cut from each of the test materials, and tested along with a control which is a piece of CELGARD® 2500 sheet from Celanese Separation Products of Charlotte, N.C. CELGARD® 2500 sheet is a microporous polypropylene sheet. Three samples are prepared for each material. The test dish is a number 60-1 Vapometer pan distributed by Thwing-Albert Instrument Company of Philadelphia, Pa. One hundred milliliters of water is poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 centimeter diameter circle having an exposed area of approximately 33.17 square centimeters. The pans are placed in a forced air oven at 100° F. (32° C.) for 1 hour to equilibrate. The oven is a constant temperature oven with external air circulating through it to prevent water vapor accumulation inside. A suitable forced air oven is, for example, a Blue M Power-O-Matic 60 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows:

Test MVTR=(grams weight loss over 24 hours)×315.5 g/m²–24 hours

The relative humidity within the oven is not specifically controlled.

Under predetermined set conditions of 100° F. (32° C.) and ambient relative humidity, the MVTR for the CELGARD® 2500 control has been defined to be 5000 grams per square meter for 24 hours. Accordingly, the control sample is run with each test and the preliminary test values are corrected to set conditions using the following equation:

MVTR=(Test MVTR/control MVTR)×(5000 g/m²–24 hours)

While the embodiments disclosed herein are presently considered preferred, various modifications and improvements can be made without departing from the spirit and scope of the invention. The scope of the invention is indicated by the appended claims, and all changes that fall within the meaning and range of equivalency are intended to be embraced therein.

I claim:

1. An absorbent composite, comprising:
    a selectively stretchable substrate which can be stretched to a greater extent in a first direction, and to a lesser extent in a second direction perpendicular to the first direction;
    a plurality of pockets in or on the selectively stretchable substrate; and
    a superabsorbent material in the pockets;
    wherein the absorbent composite can be stretched to at least 150% of an initial length in the first direction, and only to less than 150% of an initial length in the second direction before breaking;
    wherein the selectively stretchable substrate permits the pockets to push each other apart in a selected direction as the superabsorbent becomes wet and the pockets expand.

2. The absorbent composite of claim 1, wherein the composite can be stretched to at least 200% of the initial length in the first direction.

3. The absorbent composite of claim 1, wherein the composite can be stretched to at least 250% of the initial length in the first direction.

4. The absorbent composite of claim 1, wherein the composite can be stretched only to less than 125% of the initial length in the second direction.

5. The absorbent composite of claim 1, wherein the composite can be stretched only to less than 110% of the initial length in the second direction.

6. The absorbent composite of claim 1, wherein the substrate comprises a neck-bonded laminate of a neckable nonwoven web layer and an elastic layer.

7. The absorbent composite of claim 6, wherein the neckable nonwoven web comprises a spunbond web.

8. The absorbent composite of claim 6, wherein the neckable nonwoven web comprises a meltblown web.

9. The absorbent composite of claim 6, wherein the neckable nonwoven web comprises a bonded carded web.

10. The absorbent composite of claim 6, wherein the elastic layer comprises an elastic film.

11. The absorbent composite of claim 1, wherein the pockets are spaced apart at distances of about 0.05–1.5 inch (1.3–38 mm) from each other when the composite is not subjected to a stretching force.

12. The absorbent composite of claim 1, wherein the pockets are spaced apart at distances of about 0.10–1.0 inch (2.5–25 mm), when the composite is not subjected to a stretching force.

13. The absorbent composite of claim 1, wherein the pockets are spaced apart at distances of about 0.15–0.50 inch (3.8–13 mm), when the composite is not subjected to a stretching force.

14. The absorbent composite of claim 1, wherein the pockets have diameters of about 0.2–1.0 inch (5.1–25 mm) and depths of at least about 0.1 inch (2.5 mm), when the composite is not subjected to a stretching force.

15. The absorbent composite of claim 1, wherein the pockets have diameters of about 0.25–0.75 inch (6.4–19.1 mm) and depths of about 0.15–0.50 inch (3.8–13 mm), when the composite is not subjected to a stretching force.

16. A disposable absorbent article comprising a liquid permeable top sheet, a substantially liquid-impermeable back sheet, and an absorbent composite between the top sheet and the back sheet;
    the absorbent composite including a selectively stretchable substrate which can be stretched to a greater extent in a first direction, and to a lesser extent in a second direction before breaking, the second direction being perpendicular to the first direction;

the absorbent composite further including a plurality of pockets in or on the substrate material, and a superabsorbent material in the pockets;

wherein the selectively stretchable substrate permits the pockets to push each other apart in a selected direction as the superabsorbent becomes wet and the pockets expand.

17. The disposable absorbent article of claim 16, wherein the absorbent article is a diaper, and the first direction is a lateral direction extending between leg openings on a wearer.

18. The disposable absorbent garment of claim 16, wherein the absorbent composite can be stretched to at least 150% of an initial length in a first direction, and only to less than 150% of an initial length in a second direction perpendicular to the first direction.

19. The disposable absorbent article of claim 16, wherein the absorbent composite can be stretched to at least 200% of an initial length in a first direction, and only to less than 125% of an initial length in a second direction perpendicular to the first direction.

20. The disposable absorbent article of claim 16, wherein the absorbent composite can be stretched to at least 250% of an initial length in a first direction, and only to less than 110% of an initial length in a second direction perpendicular to the first direction.

21. The disposable absorbent article of claim 16, wherein the substrate comprises a neck-bonded laminate of a neckable nonwoven web and an elastic film.

22. The disposable absorbent article of claim 16, wherein the pockets together comprise about 1–100 grams of the superabsorbent.

23. The disposable absorbent article of claim 16, wherein the pockets together comprise about 3–50 grams of the superabsorbent.

24. The disposable absorbent article of claim 16, wherein the pockets together comprise about 5–15 grams of the superabsorbent.

25. The disposable absorbent article of claim 16, wherein the selectively stretchable substrate comprises the liquid permeable top sheet as a top layer of the substrate.

26. The disposable absorbent article of claim 16, wherein the selectively stretchable substrate comprises the substantially liquid-impermeable back sheet as a bottom layer of the substrate.

27. An absorbent article, comprising a liquid permeable top sheet, a substantially liquid impermeable back sheet, and an absorbent composite between the top sheet and the back sheet;

the absorbent composite including a neck-bonded laminate of a neckable nonwoven web and an elastic film;

the absorbent composite further including a plurality of pockets in or on the neck-bonded laminate, and superabsorbent material in the pockets;

wherein the absorbent composite can be stretched to at least 150% of an initial length in the first direction, and only to less than 150% of an initial length in the second direction before breaking;

wherein the neck-bonded laminate permits the pockets to push each other apart in a selected direction as the superabsorbent becomes wet and the pockets expand.

28. The absorbent article of claim 27, wherein the absorbent article is a diaper.

29. The absorbent article of claim 27, wherein the absorbent article is a training pant.

30. The absorbent article of claim 27, wherein the absorbent article is an adult incontinence garment.

31. The absorbent article of claim 27, wherein the absorbent article is swim wear.

32. The absorbent article of claim 27, wherein the absorbent article is a personal care absorbent article.

33. The absorbent article of claim 27, wherein the absorbent article is a medical absorbent article.

* * * * *